United States Patent
Hauger et al.

(10) Patent No.: US 9,526,410 B2
(45) Date of Patent: Dec. 27, 2016

(54) EYE SURGERY SYSTEM AND METHOD OF INSERTING AN INTRAOCULAR LENS

(71) Applicants: Carl Zeiss Meditec AG, Jena (DE); Carl Zeiss AG, Oberkochen (DE)

(72) Inventors: Christoph Hauger, Aalen (DE); Markus Seesselberg, Aalen (DE); Christopher Weth, Aalen (DE); Marco Wilzbach, Stuttgart (DE)

(73) Assignees: CARL ZEISS MEDITEC AG, Jena (DE); CARL ZEISS AG, Oberkochen (DE)

( * ) Notice: Subject to any disclaimer, the term of this patent is extended or adjusted under 35 U.S.C. 154(b) by 214 days.

(21) Appl. No.: 14/174,314

(22) Filed: Feb. 6, 2014

(65) Prior Publication Data
US 2014/0228948 A1   Aug. 14, 2014

(30) Foreign Application Priority Data

Feb. 8, 2013   (DE) .................. 10 2013 002 293

(51) Int. Cl.
*A61B 3/10*   (2006.01)
*A61B 3/00*   (2006.01)
(Continued)

(52) U.S. Cl.
CPC .......... *A61B 3/0025* (2013.01); *A61B 3/1005* (2013.01); *A61B 3/107* (2013.01); *A61F 2/16* (2013.01); *A61F 9/00736* (2013.01)

(58) Field of Classification Search
CPC ........ A61F 9/007; A61F 9/00736; A61B 3/00; A61B 3/10; A61B 3/107; A61B 3/0025; A61B 3/1005

(Continued)

(56) References Cited

U.S. PATENT DOCUMENTS 7,077,522 B2   7/2006  Williams
7,357,509 B2   4/2008  Williams et al.
(Continued)

FOREIGN PATENT DOCUMENTS

DE   69737242        6/1999
DE   102006005473 A1   11/2006
(Continued)

OTHER PUBLICATIONS

Office Action dated Apr. 18, 2013 in related German Patent Application No. 10 2013 002 293.2.

(Continued)

*Primary Examiner* — Eric Rosen
*Assistant Examiner* — George J Ulsh
(74) *Attorney, Agent, or Firm* — Patent Portfolio Builders PLLC

(57) ABSTRACT

A method of inserting an intraocular lens into an eye comprises: determining preoperative values of an eye; selecting an intraocular lens based on the preoperative values; inserting the intraocular lens into the eye; determining intraoperative values of the eye; providing an eye model, wherein the eye model includes plural parameters; determining the second value representing a postoperative visual defect of the eye using the eye model, wherein the preoperative values of the eye are assigned to a first subset of the plural parameters of the eye model and wherein the intraoperative values of the eye are assigned to a second subset of the plural parameters of the eye model; and correcting the position and/or the orientation of the inserted intraocular lens or inserting a different intraocular lens based on the value representing the postoperative visual defect of the eye.

16 Claims, 3 Drawing Sheets

(51) Int. Cl.
    A61F 9/007    (2006.01)
    A61B 3/107    (2006.01)
    A61F 2/16     (2006.01)
(58) Field of Classification Search
    USPC ..................................................... 623/6.12
    See application file for complete search history.

(56)               References Cited

U.S. PATENT DOCUMENTS 7,556,378 B1    7/2009  Ianchulev
    8,128,228 B2    3/2012  Van Heugten
 2008/0062384 A1    3/2008  Rombach
 2008/0165320 A1    7/2008  Heiberger
 2009/0257065 A1   10/2009  Hauger et al.
 2011/0015541 A1    1/2011  Padrick et al.
 2011/0242482 A1   10/2011  Olsen
 2012/0069303 A1    3/2012  Seesselberg et al.
 2012/0274895 A1   11/2012  van der Mooren et al.
 2013/0076960 A1    3/2013  Bublitz et al.

FOREIGN PATENT DOCUMENTS

DE      102007042571 A1    4/2008
    DE      102008047400 A1    4/2010
    DE      102010010569 A1    9/2011
    DE      102011083353 A1    3/2013
    DE      102012012281 A1   12/2013
    EP           2103249 A1    9/2009
    EP           2184005 A1    5/2010
    WO           9927334 A1    6/1999

OTHER PUBLICATIONS

Office Action dated Apr. 18, 2013 in related German Patent Application No. 10 2013 002 293.2 (English language translation).
J. Einighammer, "The Individual Virtual Eye", Dissertation Universitat Tubingen, 2008 (http://www.nbn-resolving.de/urn:nbn:de:bsz:21-opus-33012).
H.-J. Frasch et al., "Monte Carlo Methods in Raytracing Software", R.C. Juergens, Optical Design and Analysis Software II, 2002, pp. 66-77, vol. 4769, SPIE.
N. Hirnschall et al., "Predicting the Post-Operative Intraocular Lens Position Using Optical Coherence Tomography During Cataract Surgery", ARVO 2012 Annual Meeting, Poster, 2012, pp. 1.
W. Qiao et al., "Bio-Inspired Accommodating Fluidic Introcular Lens", Optics Letters, Oct. 15, 2009, pp. 3214-3216, vol. 34, No. 20.
IOLMaster 500, Defining Biometry, Carl Zeiss, Booklet, 2011, pp. 1-12.
Extended European Search Report issued in corresponding European application No. EP 14 00 0454, date of completion of the search Jan. 15, 2015.
J. Feng et al., "Constructing a Human Eye Model: The Cornea Shape Effect on Optical Imaging for the Human Eyes", 3rd International Conference on Biomedical Engineering and Informatics (BMEI), Oct. 16-28, 2010, pp. 171-173, vol. 1, IEEE.
Y. Huang et al., "Human Eye Modeling Using a Single Equation of Gradient Index Crystalline Lens for Relaxed and Accommodated States", Proc. SPIE 6342, International Optical Design Conference, 2006, pp. 1-3, Optical Society of America.
H.L. Liou et al., "Anatomically Accurate, Finite Model Eye for Optical Modeling", Journal of the Optical Society of America A, Aug. 1997, pp. 1684-1695, vol. 14, No. 8, Optical Society of America.
R. Navarro et al., "Accommodation-Dependent Model of the Human Eye with Aspherics", Journal of the Optical Society of America A, Aug. 1985, pp. 1273-1281, vol. 2, No. 8, Optical Society of America.
R. Navarro et al., "Lower- and Higher-Order Aberrations Predicted by an Optomechanical Model of Arcuate Keratotomy for Astigmatism", J Cataract Refract Surg, Jan. 2009, pp. 158-165, vol. 35, Elsevier Inc.
Zeiss Meditec, "IOLMaster with Advanced Technology Software Release 5.xx", User Manual, 2007, pp. 1-117 (retrieved from the Internet: http://www.doctor-hill.com/physicians/docs/iolmaster_5.pdf).
Partial European Search Report for corresponding European Patent Application No. 14 000 454.0, dated Feb. 9, 2015.

EYE SURGERY SYSTEM AND METHOD OF INSERTING AN INTRAOCULAR LENS

CROSS-REFERENCES TO RELATED APPLICATIONS

This application claims priority of Patent Application No. 10 2013 002 293.2, filed on Feb. 8, 2013 in Germany, the entire contents of which are incorporated by reference herein.

FIELD

The present invention relates to methods of inserting an intraocular lens into an eye and to eye surgery systems used in such methods. In a cataract surgery, the clouded crystalline lens of the eye of the patient is removed and replaced with an implant largely providing the functions of the crystalline lens and largely restoring the faculty sight of the eye. Such implant is commonly referred to as an intraocular lens (IOL). Apart from those intraocular lenses replacing the crystalline lens of the eye, there are also known so-called phakic intraocular lenses which are implanted into an eye while the crystalline lens remains in place in order to improve the performance of the eye.

BACKGROUND

The planning of a surgery for implanting an intraocular lens includes a selection of a suitable intraocular lens from a large number of different types and models of intraocular lenses available on the market. The different models of intraocular lenses may differ with respect to, for example, the refractive index of the lens material, the curvatures of the lens surfaces, the axial distance of the lens surfaces from each other, the diameter of the lens, the type of the haptics, and other properties. There are also different types of intraocular lenses, such as intraocular lenses having aspheric lens surfaces or having lens surfaces having free form surfaces without rotational symmetry, intraocular lenses providing zones with different refractive powers, and intraocular lenses including diffractive optical elements.

The selection of the type and model of the intraocular lens to be implanted into a particular eye is commonly based on preoperative values determined from the eye, such as the visual defect, the curvature of the cornea, the distance between the corneal apex and the retina of the eye, i.e. the eye length, and the distance between the corneal apex of the eye and the crystalline lens, i.e. the anterior chamber length, and other suitable values. Heuristic formulas are typically used in order to determine properties of the intraocular lens based on one or more of the above preoperative values. Examples of such formulas include the Haigis formula, the Hoffer formula, the Holladay formula and the SRK/T formula.

The selection of the type and model of the intraocular lens to be implanted into a particular eye does not always provide the desired result since the desired postoperative faculty of sight of the eye is not achieved subsequent to the surgery and after healing of incisions introduced into the cornea of the eye during the surgery.

SUMMARY

The present invention has been made in view of the above considerations.

According to some embodiments, the invention provides a method of inserting an intraocular lens and an eye surgery system which can be used in such method in order to better achieve postoperative properties of the eye.

According to some embodiments, a method of inserting an intraocular lens comprises:
(1) determining at least the following preoperative values of an eye:
  (a) a value representing a curvature of a cornea of the eye,
  (b) a value representing a distance between a corneal apex of the eye and a retina of the eye, and
  (c1) a value representing a distance between the corneal apex of the eye and a crystalline lens of the eye;
(2) selecting an intraocular lens based on the preoperative values;
(5) inserting the intraocular lens into the eye;
(6) determining at least the following intraoperative values of the eye:
  (c2) a value representing a distance between the corneal apex of the eye and the intraocular lens;
(7) providing an eye model, wherein the eye model includes at least the following parameters:
  (a) a parameter representing a curvature of a cornea of the eye,
  (b) a parameter representing a distance between a corneal apex of the eye and a retina of the eye,
  (c2) a parameter representing a distance between the corneal apex of the eye and an intraocular lens;
  (d) a parameter representing a refractive power of the intraocular lens;
(8) determining the second value representing a postoperative visual defect of the eye using the eye model, wherein:
  (a) the preoperative value representing the curvature of the cornea of the eye is assigned to the parameter of the eye model representing the curvature of the cornea of the eye,
  (b) the preoperative value representing the distance between the corneal apex of the eye and the retina of the eye is assigned to the parameter representing the distance between the corneal apex of the eye and the retina of the eye, and
  (c2) the intraoperative value representing the distance between the corneal apex of the eye and the intraocular lens is assigned to the parameter of the eye model representing the distance between the corneal apex of the eye and the intraocular lens;
  (d) a value determined based on the preoperative values or based on the selected intraocular lens is assigned to the parameter of the eye model representing the refractive power of the intraocular lens;
(9) correcting the position and/or the orientation of the inserted intraocular lens or inserting a different intraocular lens based on the second value representing the postoperative visual defect of the eye.

Both preoperatively determined values of the eye and intraoperatively determined values of the eye are used as parameters of the eye model, accordingly. The eye model is used to predict a postoperatively occurring visual defect of the eye. This prediction can be performed already during the surgery, i.e. the prediction is an intraoperative prediction such that further steps of the surgery can be planned, or an existing planning of steps of the surgery can be modified based on the intraoperatively determined postoperative visual defect of the eye. For example, the intraoperatively determined postoperative visual defect of the eye can be compared with a desired visual defect of the eye, in order to determine whether a position or an orientation of the currently inserted intraocular lens is correct or whether the selected and inserted intraocular lens should be replaced by a different intraocular lens.

Changing of the orientation of the inserted intraocular lens can be in particular useful with intraocular lenses having an astigmatic power. The correcting of the position of the inserted intraocular lens can be performed in particular in such situations in which complications occurred when the intraocular lens was inserted into the capsular bag of the eye. Replacing of the inserted intraocular lens with a different intraocular lens will occur in particular in situations in which the selection of the inserted intraocular lens based on the preoperative values and the application of one of the empirical formulas was not successful due to particular properties of the eye of the patient under surgery.

The values representing properties of the eye and the parameters of the eye model used in the method can be scalar values or tuples, wherein each tuple comprises plural scalar values. For example, the value representing the curvature of the cornea of the eye can be a radius of a sphere approximating the shape of the cornea of the eye. However, this value can also be the inverse of the radius of this sphere. Moreover, this value can be a tuple of two individual values representing the curvatures of the cornea measured in different planes. This can be in particular useful if the eye has an astigmatic visual defect. Moreover, the value representing the curvature of the cornea of the eye can be, for example, a tuple including plural coefficients resenting a Zernike polynomial representing an aspheric shape of the cornea up to a predetermined Zernike order in the usual manner.

The value representing the distance between the corneal apex and the crystalline lens of the eye can be directly measured preoperatively, i.e. before performing the surgery. This value can be also obtained by subtracting the measured value of the distance between the crystalline lens and the retina of the eye from the measured distance between the corneal apex and the retina of the eye. Thus, also the tuple of the value of the distance between the corneal apex of the eye and the retina and the value of the distance between the crystalline lens and the retina of the eye is a value representing the distance between the corneal apex and the crystalline lens of the eye. Moreover, the value representing the distance between the corneal apex and the crystalline lens of the eye can be measured relative to the main plane of the crystalline lens, the apex of the front surface of the crystalline lens, the apex of the back surface of the crystalline lens or any other element of the lens which is physically present or is a mathematical construct based on the geometry of the crystalline lens.

The eye model can be provided by plural possible methods. According to an exemplary method, the eye model is simulated using a computer and an optics software. Examples of such optics software include Code V, available from Synopsys, Inc., Pasadena, Calif., USA, and Zemax, obtainable from Radiant Zemax, LLC, Redmond, Wash., USA. Sets of parameters representing the optical properties of the simulated object, i.e. the eye, are typically supplied to the software in a suitable format. These parameters include, in particular, parameters representing the distances between interfaces, refractive indices of the materials provided between the interfaces and curvatures of the interfaces.

Suitable models of the human eye have been developed. One example is the eye model of Gullstrand. Further background knowledge and details of useful eye models can be obtained from the articles by Yanqiao Huang and Duncan T. Moore, "Human eye modeling using a single equation of gradient index crystalline lens for relaxed and accommodated states", Proc. SPIE 6342, International Optical Design Conference 2006; Jihong Feng; Hanyu Zhang; Xiaobing Wang; Aizhen Liu, "Constructing a human eye model: The cornea shape effect on optical imaging for the human eyes", 3rd International Conference on Biomedical Engineering and Informatics (BMEI), 2010, vol. 1, no., pp. 171-173, 16-18 Oct. 2010; R. Navarro; J. Santamaría; J. Bescós, "Accommodation-dependent model of the human eye with aspherics", Journal of the Optical Society of America A, Optics and image science September 1985, 2(8):1273-81; and Liou, H L, and N A Brennan, "Anatomically accurate, finite model eye for optical modeling", Journal of the Optical Society of America A, 1997, 14, no. 8: 1684-1695.

It is in particular possible to simulate the shape of the cornea of the eye using a finite element model before the shape of the cornea is inputted to the eye model. It is also possible that the calculation of the shape of the cornea using a finite element model is an intrinsic component of the eye model. An example of a finite element model simulating the shape of the cornea is illustrated in the article "Lower- and higher-order aberrations predicted by an optomechanical model of arcuate keratotomy for astigmatism" by R. Navarro et al., J Cataract Refract Surg 2009; 35: 158-165. Using of such finite element model allows to take incisions into the cornea into account which are introduced into the cornea in order to insert surgical tools into the eye, to insert the intraocular lens into the eye, or which are introduced into the cornea in order to correct visual deficiencies.

In the illustrated method, preoperatively determined values and intraoperatively determined values are assigned to the parameters of the eye model in order to determine and predict postoperative visual defects by performing calculations on the eye model. These calculations may include, for example, simulations, such as ray tracing.

According to exemplary embodiments, the intraoperatively determined values of the eye also comprise a value determined by performing a wavefront measurement on the eye. Such value can be directly used to determine the visual defect during the surgery. Such value can also be used to verify the consistency of the currently used eye model, and it is also possible to modify parameters of the currently used eye model based on the value determined by the wavefront measurement. The wavefront measurement can be performed before and/or after the insertion of the intraocular lens.

When the inserted intraocular lens has an astigmatic power, it can be advantageous if the intraoperatively determined values of the eye comprise a value obtained by performing a wavefront measurement on the eye. Values obtained by wavefront measurements readily allow to determine whether the orientation of the inserted intraocular lens is correct or should be changed.

According to exemplary embodiments, the method further comprises:

(3) applying an eye speculum to the eye before the intraocular lens is inserted into the eye, and

(10) removing the eye speculum subsequent to the correcting of the position and/or the orientation of the inserted intraocular lens or subsequent to the inserting of the intraocular lens.

The eye speculum is applied to the eye in order to maintain the eye open during the surgery. However, the eye speculum applies a certain pressure onto the cornea of the eye such that the shape of the cornea of the eye is distorted by the eye speculum. Such deformed cornea may result in that a wavefront measurement performed during the surgery detects a would-be visual defect of the eye which might result in unnecessary changes of the planning of the surgery. However, according to the illustrated method, such problens resulting from a distortion of the cornea from an applied eye speculum can be avoided since the preoperatively determined value of the curvature of the cornea is used as a parameter of the eye model for determining the postoperative visual defect of the eye.

According to further exemplary embodiments, the method further comprises:

(4) introducing at least one incision into the cornea of the eye, wherein the introducing of the incision may in particular occur before the intraocular lens is inserted into the eye, wherein the model of the eye further comprises the following parameter:

(e) a parameter representing at least one of a position, an orientation and a length of the at least one incision in the cornea of the eye, and wherein (8) the determining of the value representing the postoperative visual defect of the eye includes
  (e) a value determined based on the at least one incision introduced into the eye is assigned to the parameter of the eye model representing the at least one of the position, the orientation and the length of the at least one incision in the cornea of the eye.

An incision can be introduced into the cornea of the eye in order to insert surgical tools into the interior of the eye through the incision. The surgical tool can be, for example, an emulsifier used for removing the crystalline lens of the eye. An incision can be further introduced into the cornea of the eye in order to insert the intraocular lens into the eye. Such incisions are introduced into the cornea of the eye before the intraocular lens is inserted into the eye.

Moreover, one or more incisions can be introduced into the cornea of the eye in order to change the curvature of the cornea of the eye for influencing the faculty of sight of the eye. Such incisions can be introduced into the eye before or subsequent to the insertion of the intraocular lens into the eye.

According to exemplary embodiments, the eye model comprises a finite element model of the cornea of the eye as illustrated in the above mentioned article of R. Navarro et al.

According to further exemplary embodiments, the method is performed such that (6) the following value is determined when the intraoperative values of the eye are determined:
  (f) a value representing a centration of the intraocular lens within the eye;

wherein (7) the model of the eye comprises the following parameter:
  (f) a parameter representing a centration of the intraocular lens in the eye;

and wherein (8) when the value representing the postoperative visual defect is determined,
  (f) the determined value representing the centration of the intraocular lens within the eye is assigned to the parameter of the eye model representing the centration of the intraocular lens within the eye.

The value representing the centration of the intraocular lens within the eye can be, for example, a value defining a distance between the center of the intraocular lens from the optical axis of the eye and/or a value defining an orientation of a toric intraocular lens about the optical axis of the eye.

According to further exemplary embodiments, a method of inserting an intraocular lens into an eye comprises:

(1) determining preoperative values of an eye;
(2) selecting an intraocular lens based on the preoperative values;
(5) inserting the intraocular lens into the eye;
(6) determining intraoperative values of the eye;
(7) providing an eye model, wherein the eye model includes plural parameters;
(8) determining the second value representing a postoperative visual defect of the eye using the eye model, wherein the preoperative values of the eye are assigned to a first subset of the plural parameters of the eye model and wherein the intraoperative values of the eye are assigned to a second subset of the plural parameters of the eye model,
(9) correcting the position and/or the orientation of the inserted intraocular lens or inserting a different intraocular lens based on the value representing the postoperative visual defect of the eye.

According to particular embodiments herein, the preoperative values comprise one or more values selected from the following values:

(a) a value representing a curvature of a cornea of the eye,
(b) a value representing a distance between a corneal apex of the eye and a retina of the eye, and
(c1) a value representing a distance between the corneal apex of the eye and a crystalline lens of the eye.

According to particular embodiments herein, the intraoperative values comprise one or more values selected from the following values:

(a) a value representing a curvature of a cornea of the eye,
(b) a value representing a distance between a corneal apex of the eye and a retina of the eye,
(c2) a value representing a distance between the corneal apex of the eye and the intraocular lens,
(e) a value representing at least one of a position, an orientation and a length of the at least one incision in the cornea of the eye, and
(f) a value representing a centration of the intraocular lens within the eye.

According to some embodiments of the method, a first eye model instance includes a representation of the cornea based on the intraoperative value representing the curvature of the cornea;

wherein a second eye model instance includes a representation of the cornea based on the preoperative value representing the curvature of the cornea;

wherein the determining of the intraoperative values includes a performing of a wavefront measurement for determining a first set of light rays outside of the eye;

wherein the determining of the second value representing a postoperative visual defect of the eye comprises:
  calculating a second set of light rays inside the eye by extrapolating the light rays of the first set of light rays using the first eye model instance,
  calculating a third set of light rays outside the eye by extrapolating the light rays of the second set of light rays using the second eye model instance, and
  determining the second value representing a postoperative visual defect of the eye based on the third set of light rays.

According to exemplary embodiments, an eye surgery system comprises
a user interface;
a measuring system configured to determine at least preoperative values and intraoperative values of an eye;
a first computing module configured to determine a first value based on preoperative values, wherein the first value represents a property of an intraocular lens;
a second computing module configured to determine a second value based on a simulation performed on an eye model, wherein the second value represents a postoperative visual defect of an eye, and wherein the eye model includes plural parameters;

a controller configured
(1) to receive preoperative values,
(2) to trigger the first computing module to determine the first value representing the property of the intraocular lens, based on the preoperative values,
(5) to trigger the user interface to display the first value representing the property of the intraocular lens,
(6) to trigger the measuring system to determine intraoperative values,
(8) to trigger the second computing module to determine the second value representing the postoperative visual defect of the eye, wherein the preoperative values of the eye are assigned to a first subset of the plural parameters and wherein the intraoperative values of the eye are assigned to a second subset of the plural parameters of the eye model, and
(9) to trigger the user interface to display the second value representing the postoperative visual defect of the eye.

The eye surgery system can be an integral system or a distributed system. When the eye surgery system is embodied as a distributed system, the measuring system for determining the preoperative values can be different from and located at a different site than the measuring system for determining the intraoperative values. Moreover, the controller can be embodied as a distributed system comprising plural components located at different sites, wherein the components are connected using suitable data connections, such as a computer network. The first computing module and the second computing module can be embodied as software modules running on one or more computers which can be integrated with the controller or located outside of the controller and connected with the controller via a suitable data connection.

The first computing module can be configured, for example, to determine the first value representing the intraocular lens using the Haigis formula, the Hoffer formula, the Holladay formula, the SRK/T formula or other suitable computing methods. The first value representing the intraocular lens may include, for example, a refractive index lens of the intraocular lens, an identifier designating the material of which the lens of the intraocular lens is made, curvature of one or both surfaces of the intraocular lens and other data. The first value representing the intraocular lens may also include an identifier designating the type or model of the intraocular lens to be used, such as a trade name and a product designator under which the respective intraocular lens is available on the market.

The second computing module can be configured to perform an optics software, such as Code V or Zemax. The second computing module can be further configured to run a finite element model simulating the shape of the cornea of the eye.

According to further exemplary embodiments, the controller can be configured to wait for a predetermined user input via the user interface before the measuring system is triggered to determine the preoperative values, and/or wherein the controller is configured to wait for a predetermined user input via the user interface before the measuring system is triggered to determine the intraoperative values.

According to further exemplary embodiments, the measuring system includes at least one of a keratoscope and an OCT measuring device for determining the value representing the curvature of the cornea of the eye.

According to further exemplary embodiments, the measuring system comprises at least one of an OCT measuring device, an ultrasound measuring device and an interface measuring device for determining the value representing the distance between the corneal apex of the eye and the retina of the eye.

According to further exemplary embodiments, the measuring system comprises at least one of an OCT measuring device and an interface measuring device for determining at least one of the value representing the distance between the corneal apex of the eye and the crystalline lens of the eye and/or the value representing the distance between the corneal apex of the eye and the intraocular lens.

According to further exemplary embodiments, the measuring system comprises at least one of a wave front measuring device and an ametropia measuring device for determining the value representing the centration of the intraocular lens within the eye.

BRIEF DESCRIPTION OF THE DRAWINGS

The forgoing as well as other advantageous features of the disclosure will be more apparent from the following detailed description of exemplary embodiments with reference to the accompanying drawings. It is noted that not all possible embodiments necessarily exhibit each and every, or any, of the advantages identified herein.

DETAILED DESCRIPTION OF EXEMPLARY EMBODIMENTS

Figure 1:
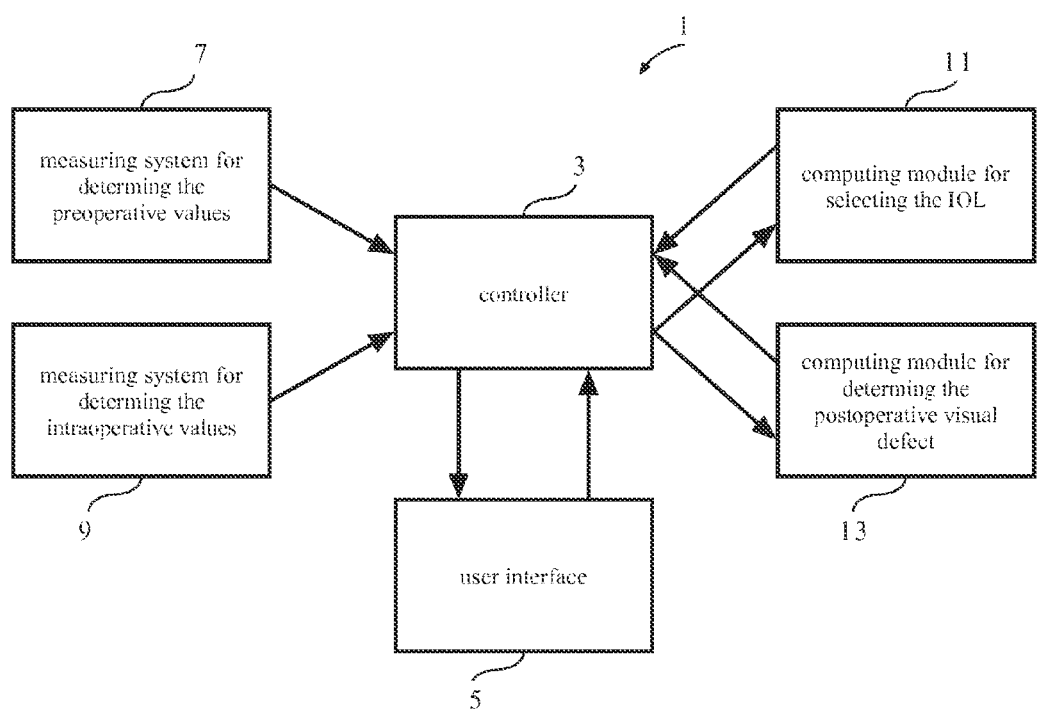
FIG. 1 is a schematic illustration of an eye surgery system according to an embodiment.

In the exemplary embodiments described below, components that are alike in function and structure are designated as far as possible by alike reference numerals. Therefore, to understand the features of the individual components of a specific embodiment, the descriptions of other embodiments and of the summary of the disclosure should be referred to.

FIG. 1 is a block diagram schematically illustrating components of an eye surgery system 1. A method of inserting an intraocular lens into an eye which will be illustrated with reference to FIG. 2 in more detail below can be performed using the eye surgery system 1.

The eye surgery system 1 comprises a controller 3, a user interface 5, a first measuring system 7 for determining preoperative values of an eye, a second measuring system 9 for determining intraoperative values of the eye, a first computing module 11 for selecting an intraocular lens, and a second computing module 13 for determining a postoperative visual defect.

The eye surgery system 1 can be embodied as a distributed system in which the first measuring system 7 and the second measuring system 9 are separate systems located at different sites and which can be used, for example, by different operators at different times in order to perform measurements on the eye of a patient. Measuring values generated by the first measuring system 7 and the second measuring system 9 are transmitted to the controller 3 as measurement data. The measurement data can be temporally stored in suitable memories available at the measuring systems 7 and 9, at the controller 3 or at some other location. Moreover, also the controller 3 can be embodied as a distributed system such that, for example, portions of the controller are integrated with one or both measuring systems 7 and 9, or portions of the controller can be located separate from the measuring systems 7 and 9.

The user interface 5 includes, for example, a display, such as a computer monitor, for outputting and displaying data, and an input device, such as a keyboard or a mouse, for inputting data. Also the user interface can be embodied as a distributed system, such that a portion of the functions of the user interface are integrated with the first measurement system 7, other portions of the functions are integrated with the measurement system 9, and further portions of the functions are integrated with a further system, such as, for example, the controller 3.

The first computing module 11 and the second computing module 13 are embodied as software modules running on one or more computers, wherein the one or more computers may also run additional software providing functions of the controller 3, the user interface 5, the first measuring system 7 and the second measuring system 9.

The method of inserting an intraocular lens (IOL) into an eye using the eye surgery system 1 will be illustrated in more detail with reference to the flowchart of FIG. 2.

It is a purpose of the method to insert an intraocular lens into an eye of a patient. The inserting of an intraocular lens into the eye can be advantageous if the crystalline lens of the eye shows a cataract such that the clouded crystalline lens is to be removed and replaced by an implant, i.e. the intraocular lens. The insertion of an intraocular lens can be further desirable if the eye has a visual defect, wherein it is not possible to compensate the visual defect using eye glasses or wherein the patient intends to compensate the visual defect without wearing eye glasses. In such situations, an implant, which is commonly referred to as a phakic intraocular lens, can be inserted into the eye in addition to the crystalline lens of the eye which remains in the eye.

In such method of inserting an intraocular lens into the eye it is at first necessary to select a suitable type of intraocular lens. Plural different types of intraocular lenses are available on the market, and these lenses differ with respect to the manufacturer, the optical properties, such as refractive power, and haptics. The currently available types of intraocular lenses are known to the eye surgery system and stored in a data base 51 which can be accessed by the controller 3 and/or the first computing module 11.

Measurements on the eye are performed in order to select a suitable type of intraocular lens for a particular eye. The optical properties of the eye are determined using these measurements such that the suitable type of intraocular lens can be selected based on these measurements such that the eye has a desired faculty of sight or desired visual defect subsequent to the surgery.

Before the surgery, measurements are performed on the eye using the first measuring system before the surgery in a step 53 in order to obtain preoperative values. For performing the measurement, an operator positions the patient relative to the first measuring system 7 such that the desired measurement on the eye of the patient can be performed using the measuring system 7. The operator may initiate the measurement by submitting a predetermined user input to the user interface, wherein the controller is waiting for this input before it triggers the measuring system to perform the measurement.

The preoperative values represent properties of the eye before the surgery. A plurality of values are generated in step 53. In particular, these values include a value 55 representing the curvature of the cornea of the eye, a value 57 representing a distance between the corneal apex and the crystalline lens of the eye, and a value 59 representing a distance between the corneal apex and the retina of the eye.

The first measuring system 7 may comprise plural devices for determining these values. For example, the curvature of the cornea can be measured using a keratoscope or an OCT-device, the distance between the corneal apex and the crystalline lens can be measured, for example, using an OCT-device or an interface measuring device, and the distance between the corneal apex and the retina can be measured using an OCT-device, an ultrasound device and an interface measuring device. These values can be measured in particular using a measuring system available under the trade name IOL-Master from Carl Zeiss Meditec, Jena, Germany.

Figure 2:
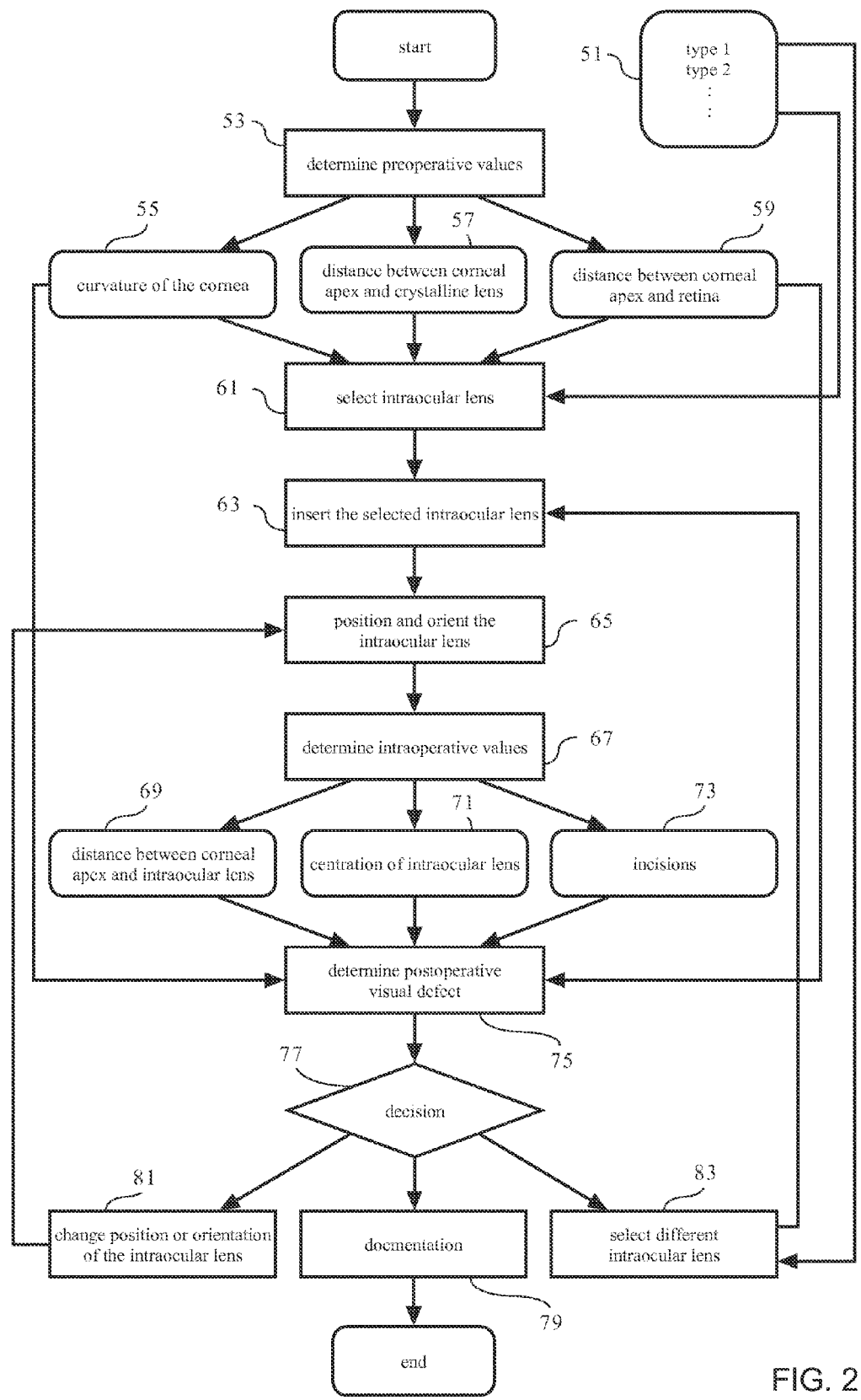
FIG. 2 is a flowchart illustrating a method of inserting an intraocular lens into an eye, wherein the method can be performed using the eye surgery system shown in FIG. 1.

In addition to the values 55, 57 and 59 shown in FIG. 2, other preoperative values representing properties of the eye can be determined before performing the surgery. For example, a value representing the visual defect of the eye can be measured using a wavefront measuring system, such as a system known from EP 2 103 249 A1.

A suitable type of intraocular lens is determined in a step 61, based on the preoperative values 55, 57, 59 and additional values, if desired. Such additional values may include further preoperative values determined before the surgery has started, and the additional values may also include values determined by intraoperative measurements performed after the surgery has started. For example, a wavefront measurement can be performed after the crystalline lens of the eye has been removed. Therefore, the determination of the intraocular lens can be based on both preoperative values and postoperative values. The selection can be performed using the first computing module 11. For this purpose, the controller 3 transmits the preoperative values 55, 57, 59, and additional values, if desired, to the computing module 11. The computing module 11 has access to the data base 51 storing properties of the available intraocular lenses. The computing module 11 then selects, based on the preoperative values, that type of intraocular lens, which achieves or approximately achieves the desired postoperative faculty of sight if an instance of this type of intraocular lens was inserted into the eye. The computing module 11 performs suitable calculations in order to select the correct type of intraocular lens. These calculations may include an evaluation of suitable formulas, such as, for example, the Haigis formula, the Hoffer formula, the Holladay formula and the SRK/T formula. Moreover, the first computing module may perform optical calculations using a suitable software, such as, for example, Code V or Zemax. The first calculation module 11 transmits a result of these calculations to the controller 3. The result is transmitted as data representing the suitable type of intraocular lens. These data may comprise optical properties of the intraocular lens, such as it's power, or a product designator of the selected type of intraocular lens.

Thereafter, the controller instructs the user interface 5 to display the selected type of intraocular lens, such that an operator may perceive the type of intraocular lens and obtain an instance of the selected type of intraocular lens from a stock, for example.

The selected intraocular lens is inserted into the eye of the patient in a step 63. When the crystalline lens of the eye has developed a cataract, the clouded crystalline lens is removed before the intraocular lens is inserted. For this purpose, one or more incisions are inserted into the cornea of the eye, and the distal end of an emulsifier is inserted into the eye in order to disintegrate the crystalline lens and remove the portions of the crystalline lens by suction. The intraocular lens is inserted into the eye through a further incision introduced into the cornea. Further incisions can be introduced into the cornea of the eye in order to affect the curvature of the cornea in order to reduce a visual defect of the eye.

Subsequent to the inserting of the intraocular lens into the eye, the lens is positioned in the capsular bag or in front of the capsular bag and rotated as required, in a step 65.

It is now desirable to verify a result of the surgery performed so far. If the result conforms with the desired result, the surgery can be terminated, or the surgery can be continued by performing further steps in order to improve the result, if the confirmed result does not conform with the desired result. Measurements are performed on the eye using the second measuring system 9 in a step 67 during the surgery, in order to generate intraoperative values representing properties of the eye. The operator may initiate the measurement by submitting a predetermined user input to the user interface, wherein the controller is waiting for this input before it triggers the second measuring system 9 to perform the measurement of the intraoperative values.

The intraoperative values comprise a value 69 representing a distance between the corneal apex of the eye and the intraocular lens inserted into the eye, a value 71 representing a centration of the inserted intraocular lens within the eye, and a value 73 representing a configuration and a geometry of incisions introduced into the cornea of the eye.

The second measuring system may comprise plural devices for determining the values 69, 71 and 73. For example, the value 69 representing the distance between the corneal apex and the intraocular lens using an OCT-device, an ultrasound device or an interface measuring device. An OCT-device or a wavefront measuring device, such as the device illustrated in EP 2 103 249 A1, can be used, for example, to determine the value 71 representing the centration of the intraocular lens within the eye.

The value 73 representing the incisions introduced into the cornea of the eye can be inputted into the system via the user interface 5, for example. For this purpose, the value 73 typically comprises plural individual values representing positions, orientations, lengths and curvatures of the incisions.

A value representing the postoperative visual defect of the eye is determined in a step 75 using the second calculation module 13 based on the intraoperative values 69, 71, 73 and at least some of the preoperative values. The preoperative values used for this calculation may in particular include the value 55 representing the curvature of the cornea and the value 59 representing the distance of the corneal apex from the retina of the eye. For this purpose, the intraoperative values 69, 71, 73 and preoperative values 55, 59 are supplied to the second computing module 13. The computing module 13 comprises optical software, such as Code V or Zemax, for determining the optical properties of the eye after the surgery based on the preoperative values and the intraoperative values. The second computing module 13 may further comprise a finite element software in order to predict the shape of the cornea.

A decision step 77 is performed based on the determined postoperative visual defect in order to decide how the surgery is to proceed. If the determined postoperative visual defect conforms with the desired visual defect, it can be expected that the postoperative properties of the eye will be as expected. In such situation, the surgery can be terminated by performing the necessary steps and completing a documentation of the surgery in a step 79. It is possible, based on such documentation, to compare the predicted postoperative visual defect determined in step 75 with the visual defect the eye has developed after, for example, a couple of weeks. It is possible to improve the eye model used in the second calculation module 13 based on such comparisons.

The postoperative visual defect determined in step 75 may indicate that the inserted intraocular lens is not correctly positioned or oriented within the eye. In such situation, the surgery may proceed with a step 81 in which suitable information is displayed using the user interface 5. It is then possible to correct the position and/or orientation of the intraocular lens within the eye in a step 65. It is then possible to repeat the processing using the determining of the intraoperative values in step 67 and the determination of the postoperative visual defect in the step 75, and to repeat the decision step 77 until the surgery can be terminated when the desired result is achieved.

The determined postoperative visual defect may also indicate that the inserted intraocular lens may not achieve the desired result such that it is advantageous to use a different type of intraocular lens in order to achieve a better result. The processing will then proceed from the decision step 77 to step in which a different type of intraocular lens is selected using the calculation module 11. For this purpose, the preoperative values and the intraoperative values are supplied to the calculation module 11, and a suitable type of intraocular lens is selected based on these preoperative values and intraoperative values as illustrated above with reference to step 61. Thereafter, the inserted intraocular lens is removed from the eye, and an intraocular lens of the type selected in the step 83 is inserted into the eye in the step 63. Thereafter, the step 65 of positioning and orientating the intraocular lens, the step 67 of determining the intraoperative values, the step of determining the postoperative visual defect and the decision step 77 can be repeated until the desired result of the surgery can be expected such that the surgery can be terminated with step 79.

An example of computations performed by the second computing module will be illustrated with reference to FIGS. 3A, 3B and 3C below.

It is assumed that the surgery has proceeded to a situation where the intraocular lens has been inserted into the eye of the patient such that it is now desired to determine the postoperative visual defect or faculty of sight of the eye. The visual defects of an eye can be measured with a high accuracy by using a wavefront measurement. However, it is rarely possible to precisely determine the postoperative visual defect by a wavefront measurement performed on the eye of the patient in the assumed situation of the surgery. A main reason is the fact that the shape of the cornea of the eye under surgery is different from the shape of the cornea found a couple of weeks after the surgery. The cornea of the eye under surgery is distorted relative to the cornea after termination of the surgery. There are plural reasons for such distorted cornea.

One reason is the presence of an eye speculum applying a pressure to the cornea and deforming its shape. A further reason is the intraocular pressure which has changed due to the surgery and is different from the intraocular pressure when it is restored to the natural intraocular pressure some time after the surgery. The curvature of the cornea depends on the intraocular pressure. The incisions introduced into the cornea are a further reason for the distortion of the cornea of the eye under surgery. A healing process of the incisions will change the surface tension of the cornea and its shape accordingly.

In the present example, a wavefront measurement is still performed by using a wavefront measurement device of the measuring system. Based on the measured wavefront, it is possible to determine light rays corresponding to the measured wavefront, wherein these light rays can be used in an optical simulation of a model eye. These light rays are orthogonal to the measured wavefront.

The intraoperative value of the curvature of the cornea of the eye is also measured using the measuring system. FIG. 3A schematically illustrates an instance 20 of the eye model and a set of light rays M1 outside of the eye. The eye model includes a retina 21, a vitreous body 22, an intraocular lens 23, an anterior chamber 24 and a cornea 25. The eye model instance 20 is defined by the values assigned to the parameters of the eye model. The eye model instance 20 shown in FIG. 3A includes a representation of the cornea having a shape or curvature as measured using the measuring system in the present stage of the surgery. Thus, the value of the measured curvature of the cornea is assigned to the parameter of the eye model representing the curvature of the cornea. Arrows 26 in FIG. 3A represent forces applied to the cornea by the eye speculum such that the shape of the cornea is distorted.

Figure 3A:
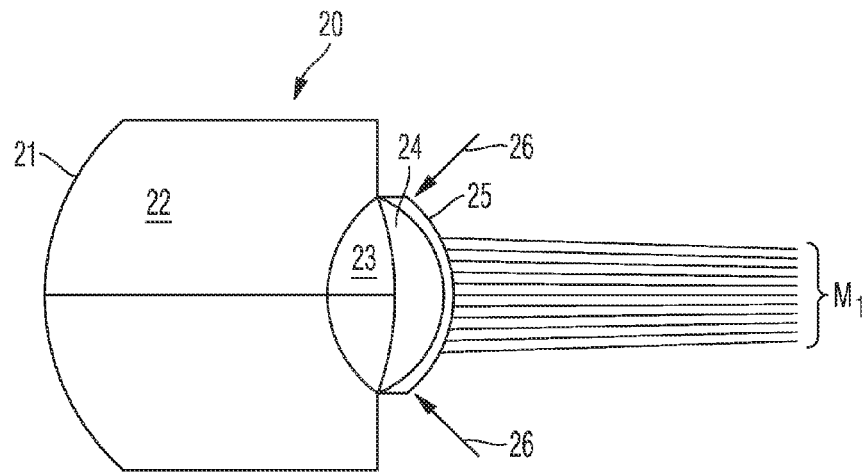
FIGS. 3A, 3B, 3C are schematic illustrations of an optical simulation using an eye model.
Figure 3B:
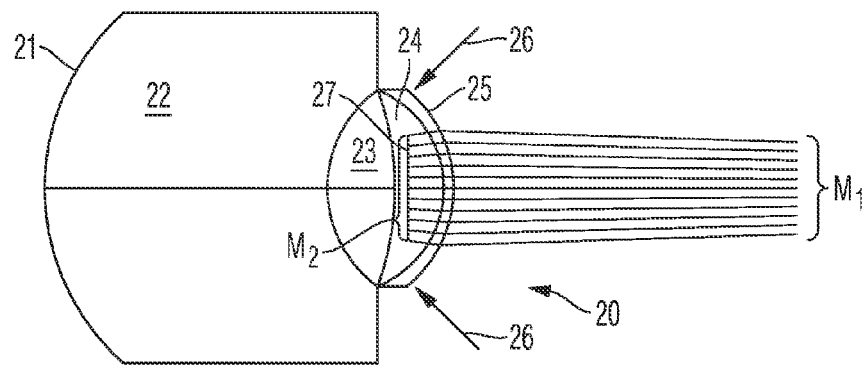

The set of lights rays M1 as determined from the intraoperative wavefront measurement extend to the surface of the cornea in FIG. 3A. A raytracing software is then used to extrapolate the light rays of the set M1 into the interior of the eye. This is illustrated in FIG. 3B which shows the same eye model instance 20 and set of light rays M1 as FIG. 3A, wherein an extrapolated set of light rays M2 is shown in the interior of the eye. In the present example, a reference plane 27 is defined in the anterior chamber 24 of the eye model, and the raytracing software is used to calculate the rays of the set M2 until they are incident on the reference plane 27.

Figure 3C:
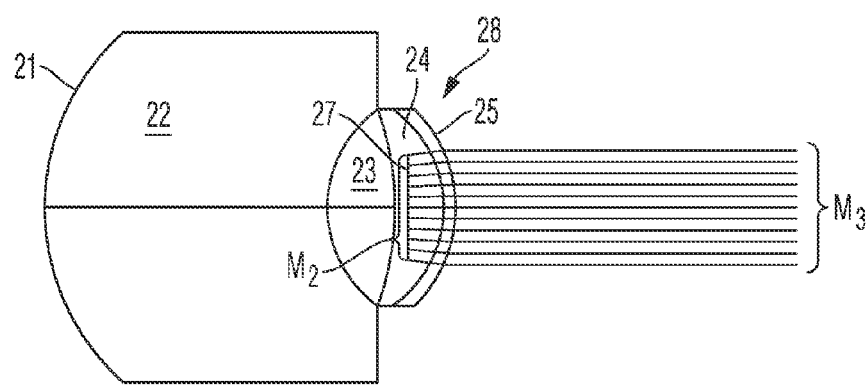

Thereafter, the eye model instance is changed to a different eye model instance 28 shown in FIG. 3C. The value of the parameter representing the curvature of the cornea 25 of the eye model instance 28 is the preoperative value of the curvature of the cornea. This is based on the assumption that the intraoperatively measured curvature of the cornea differs from the postoperative curvature of the cornea and that the preoperatively determined value of the curvature of the cornea better approximates the postoperative curvature of the cornea. Apart from the curvature of the cornea 25, the eye model instance 28 has the same values assigned to its parameters as the eye model instance 20. Moreover, the reference plane 27 in the eye model instance 28 is located at a same location relative to the intraocular lens 23 as in the eye model instance 20. Thereafter, the raytracing software is used to extrapolate the set of rays M2 from the interior of the eye to the outside of the eye. These extrapolated light rays are shown in FIG. 3C as a set of light rays M3. The set of extrapolated light rays M3 is then used to determine the postoperative visual defect of the eye. It is assumed that this calculated postoperative visual defect approximates the true visual defect established a couple of weeks after the surgery better than the visual defect directly determined from the intraoperatively measured wave front.

Based on this result it is then possible to decide whether the position of the implanted intraocular lens within the eye should be corrected, the orientation of the implanted intraocular lens should be corrected or whether the implanted intraocular lens should be replaced by a different type of intraocular lens.

The accuracy of the prediction of the postoperative visual defect of the eye can be further improved if the value of the curvature of the cornea used in the second eye model instance 28 is based on the preoperative value of the curvature of the cornea but corrected by taking the incisions in the cornea into account in order to better predict the postoperative shape of the cornea. Background information for such prediction of the postoperative shape of the cornea can be obtained from the article of R. Navarro et al. mentioned above.

It is further possible to measure the intraocular pressure during the surgery and to take the intraoperative value of the intraocular pressure into account when the postoperative curvature of the cornea is determined for the second eye model 28.

In the above example, the set of light rays M1 is extrapolated into the interior of the eye up to reference plane 27 which is located in the anterior chamber 24 of the eye. It is, however, also possible to locate the reference plane at some other location within the eye. For example, the reference plane can be located within the vitreous body 22 such that the set of light rays M2 also traverses the intraocular lens 23. This can be in particular advantageous in situations where the intraocular lens has an astigmatic power and a change of the orientation of the intraocular lens is considered based on the result of the measurement.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the spirit and scope of the present disclosure as defined in the following claims.

What is claimed is:

1. An eye surgery system, comprising:
    a user interface;
    a measuring system including one or more measuring devices, the measuring system configured to determine at least preoperative values and intraoperative values of an eye;
    one or more computers configured to execute a first computing module configured to determine a first value based on preoperative values, wherein the first value represents a property of an intraocular lens;
    the one or more computers configured to execute a second computing module configured to determine a second value based on a simulation performed on an eye model, wherein the second value represents a postoperative visual defect of an eye, and wherein the eye model includes plural parameters; and
    a controller configured
        to trigger the measuring system to determine preoperative values including a value representing a curvature of a cornea of the eye,
        to trigger the first computing module to determine the first value representing the property of the intraocular lens, based on the preoperative values,
        to trigger the user interface to display the first value representing the property of the intraocular lens,
        to trigger the measuring system to determine intraoperative values,
        to trigger the second computing module to determine the second value representing the postoperative visual defect of the eye, wherein the preoperative values of the eye are assigned to a first subset of the plural parameters and wherein the intraoperative values of the eye are assigned to a second subset of the plural parameters of the eye model, and to trigger the user interface to display the second value representing the postoperative visual defect of the eye.

2. The eye surgery system according to claim 1, wherein the controller is configured to wait for a predetermined user input via the user interface before the measuring system is triggered to determine the preoperative values, and/or wherein the controller is configured to wait for a predetermined user input via the user interface before the measuring system is triggered to determine the intraoperative values.

3. The eye surgery system according to claim 1, wherein the preoperative values further comprise one or more values selected from the following values:
   a value representing a distance between a corneal apex of the eye and a retina of the eye, and
   a value representing a distance between the corneal apex of the eye and a crystalline lens of the eye.

4. The eye surgery system according to claim 1, wherein the intraoperative values comprise one or more values selected from the following values:
   a value representing a curvature of a cornea of the eye,
   a value representing a distance between a corneal apex of the eye and a retina of the eye, and
   a value representing a distance between the corneal apex of the eye and the intraocular lens of the eye,
   a value determined based on at least one incision introduced into the cornea of the eye,
   a value representing a centration of the intraocular lens within the eye, and
   a wavefront measurement data.

5. An eye surgery system, comprising:
   a user interface;
   a measuring system including one or more measuring devices, the measuring system configured to determine at least the following values of an eye:
      a value representing a curvature of a cornea of the eye,
      a value representing a distance between a corneal apex of the eye and a retina of the eye, and
      a value representing a distance between the corneal apex of the eye and a crystalline lens of the eye, and
      a value representing a distance between the corneal apex of the eye and the intraocular lens;
   one or more computers executing a first computing module configured to determine a first value representing a property of an intraocular lens, wherein the first value is determined based on at least the following values:
      the value representing the curvature of a cornea of the eye,
      the value representing the distance between the corneal apex of the eye and the retina of the eye, and
      the value representing the distance between the corneal apex of the eye and the crystalline lens of the eye;
   the one or more computers executing a second computing module configured to determine a second value representing a postoperative visual defect of the eye, wherein the second value is determined based on a simulation performed on an eye model, and wherein the eye model includes at least the following parameters:
      a parameter representing a curvature of a cornea of the eye,
      a parameter representing a distance between a corneal apex of the eye and a retina of the eye, and
      a parameter representing a distance between the corneal apex of the eye and a crystalline lens of the eye,
      a parameter representing a distance between the corneal apex of the eye and the intraocular lens of the eye;
      a parameter representing a refractive power of the intraocular lens; and
   a controller configured
      to receive at least the following preoperative values determined by the measuring system:
         the value representing the curvature of the cornea of the eye,
         the value representing the distance between the corneal apex of the eye and the retina of the eye, and
         the value representing the distance between the corneal apex of the eye and the crystalline lens of the eye;
      to trigger the first computing module to determine the first value representing the property of the intraocular lens, based on the determined preoperative values;
      to trigger the user interface to display the first value representing the property of the intraocular lens;
      to trigger the measuring system to determine at least the following intraoperative values:
         the value representing the distance between the corneal apex of the eye and the intraocular lens;
      to trigger the second computing module to determine the second value representing the postoperative visual defect of the eye, wherein:
         the preoperative value representing the curvature of the cornea of the eye is assigned to the parameter of the eye model representing the curvature of the cornea of the eye,
         the preoperative value representing the distance between the corneal apex of the eye and the retina of the eye is assigned to the parameter representing the distance between the corneal apex of the eye and the retina of the eye, and
         the intraoperative value representing the distance between the corneal apex of the eye and the intraocular lens is assigned to the parameter of the eye model representing the distance between the corneal apex of the eye and the intraocular lens;
      to trigger the user interface to display the second value representing the postoperative deficiency of the eye.

6. The eye surgery system according to claim 5, wherein the controller is configured to wait for a predetermined user input via the user interface before the measuring system is triggered to determine the preoperative values, and/or wherein the controller is configured to wait for a predetermined user input via the user interface before the measuring system is triggered to determine the intraoperative values.

7. The eye surgery system according to claim 5, wherein the eye model further comprises the following parameter:
   a parameter representing at least one of a position, an orientation and a length of at least one incision introduced into the cornea of the eye,
   and wherein the controller is further configured
      to receive a value, via the user interface, representing at least one of a position, an orientation and a length of at least one incision introduced into the cornea of the eye, and
      to trigger the second computing module to determine the second value representing the postoperative visual defect of the eye, wherein:
         the value representing the at least one of the position, the orientation and the length of the at least one incision introduced into the cornea of the eye is assigned to the parameter of the eye model representing the at least one of the position, the orientation and the length of the at least one incision introduced into the cornea of the eye.

8. The eye surgery system according to claim 5, wherein the measuring system is further configured to determine the following intraoperative value from the eye:
a value representing a centration of the intraocular lens within the eye;
wherein the eye model further comprises the following parameter:
a parameter representing a centration of the intraocular lens within the eye;
and wherein the controller is further configured
to trigger the second computing module to determine the second value representing the postoperative visual defect of the eye, wherein:
the value representing the centration of the intraocular lens within the eye is assigned to the parameter of the eye model representing the centration of the intraocular lens within the eye.

9. The eye surgery system according to claim 1, wherein the measuring system includes at least one of a keratoscope and an OCT measuring device for determining the value representing the curvature of the cornea of the eye.

10. The eye surgery system according to claim 1, wherein the measuring system comprises at least one of an OCT measuring device, an ultrasound measuring device and an interface measuring device for determining the value representing the distance between the corneal apex of the eye and the retina of the eye.

11. The eye surgery system according to claim 1, wherein the measuring system comprises at least one of an OCT measuring device and an interface measuring device for determining at least one of the value representing the distance between the corneal apex of the eye and the crystalline lens of the eye and/or the value representing the distance between the corneal apex of the eye and the intraocular lens.

12. The eye surgery system according to claim 1, wherein the measuring system comprises at least one of a wave front measuring device and an ametropia measuring device for determining the value representing the centration of the intraocular lens within the eye.

13. A method of inserting an intraocular lens into an eye, the method comprising: determining preoperative values of an eye, the preoperative values including a value representing a curvature of a cornea of the eye; selecting an intraocular lens based on the preoperative values; inserting the intraocular lens into the eye; determining intraoperative values of the eye; providing an eye model, wherein the eye model includes plural parameters; determining the second value representing a postoperative visual defect of the eye using the eye model, wherein the preoperative values of the eye are assigned to a first subset of the plural parameters of the eye model and wherein the intraoperative values of the eye are assigned to a second subset of the plural parameters of the eye model; and correcting the position and/or the orientation of the inserted intraocular lens or inserting a different intraocular lens based on the value representing the postoperative visual defect of the eye.

14. The method according to claim 13, wherein the preoperative values further comprise one or more values selected from the following values:
a value representing a distance between a corneal apex of the eye and a retina of the eye, and
a value representing a distance between the corneal apex of the eye and a crystalline lens of the eye.

15. The method according to claim 13, wherein the intraoperative values comprise one or more values selected from the following values:
a value representing a curvature of a cornea of the eye,
a value representing a distance between a corneal apex of the eye and a retina of the eye,
a value representing a distance between the corneal apex of the eye and the intraocular lens,
a value representing at least one of a position, an orientation and a length of the at least one incision in the cornea of the eye, and
a value representing a centration of the intraocular lens within the eye.

16. The method according to claim 13, wherein the eye model comprises a first eye model instance and a second eye model instance; wherein the first eye model instance includes a representation of the cornea based on the intraoperative value representing the curvature of the cornea; wherein the second eye model instance includes a representation of the cornea based on the preoperative value representing the curvature of the cornea; wherein the determining of the intraoperative values includes a performing of a wavefront measurement for determining a first set of light rays outside of the eye; wherein the determining of the second value representing a postoperative visual defect of the eye comprises:
calculating a second set of light rays inside the eye by extrapolating the light rays of the first set of light rays using the first eye model instance,
calculating a third set of light rays outside the eye by extrapolating the light rays of the second set of light rays using the second eye model instance, and
determining the second value representing a postoperative visual defect of the eye based on the third set of light rays.

* * * * *